(12) United States Patent
De Vries et al.

(10) Patent No.: US 8,042,944 B2
(45) Date of Patent: Oct. 25, 2011

(54) APPARATUS AND METHOD FOR OBSERVING AN EYE, AS WELL AS OCT-MODULE

(75) Inventors: Haaije Rimmer De Vries, Rotterdam (NL); Petrus Jacobus Wilhelmus Gelissen, Nieuwerkerk aan den IJssel (NL); Takefumi Hayashi, Saitama (JP)

(73) Assignee: Topcon Europe Medical B.V., Capelle Aan Den Ijssel (NL)

( * ) Notice: Subject to any disclaimer, the term of this patent is extended or adjusted under 35 U.S.C. 154(b) by 0 days.

(21) Appl. No.: 12/532,119

(22) PCT Filed: Mar. 20, 2008

(86) PCT No.: PCT/NL2008/050158
§ 371 (c)(1),
(2), (4) Date: Sep. 18, 2009

(87) PCT Pub. No.: WO2008/115060
PCT Pub. Date: Sep. 25, 2008

(65) Prior Publication Data
US 2010/0033676 A1  Feb. 11, 2010

(30) Foreign Application Priority Data
Mar. 20, 2007 (EP) .................... 07104507

(51) Int. Cl.
*A61B 3/10* (2006.01)
(52) U.S. Cl. ...................... 351/221; 351/206
(58) Field of Classification Search .......... 351/206, 351/221
See application file for complete search history.

(56) References Cited

U.S. PATENT DOCUMENTS

| | | | |
|---|---|---|---|
| 6,485,413 B1 * | 11/2002 | Boppart et al. | 600/160 |
| 2004/0021874 A1 | 2/2004 | Shimmick | |
| 2007/0258095 A1 * | 11/2007 | Olivier et al. | 356/479 |
| 2007/0263171 A1 * | 11/2007 | Ferguson et al. | 351/206 |
| 2010/0142780 A1 * | 6/2010 | Yasuno et al. | 382/131 |

FOREIGN PATENT DOCUMENTS
WO   03/086180 A2   10/2003

OTHER PUBLICATIONS

Hellmuth, T., "Optische Kohaerenztomographie in Der Ophthalmoskopie (Optical Coherence Tomography in Ophthalmoscopy)," Technisches Messen TM, R. Oldenbourg Verlag. Munchen DE, vol. 63, No. 61, Jun. 1, 1996, pp. 241-246.
International Search Report mailed Jun. 5, 2008, in connection with Application No. PCT/NL2008/050158.

* cited by examiner

*Primary Examiner* — Hung Dang
(74) *Attorney, Agent, or Firm* — Fliesler Meyer LLP

(57) ABSTRACT

An apparatus for observing an eye comprises an imaging device (9) that is provided with a magnification unit (11) and an observation unit (10). The magnification unit (11) has an objective lens (12) for receiving observation light rays from the eye. The apparatus includes an optical coherence tomography (OCT) system (15) comprising an OCT light source (16) for emitting OCT light, as well as splitting means (17) for splitting the OCT light into a reference beam and a sample beam. The OCT system (15) comprises transferring means (33) for directing the sample beam from the splitting means through the objective lens to the eye. The OCT system comprises an OCT module (19) that is detachably connected between the magnification unit (11) and the observation unit (10).

10 Claims, 4 Drawing Sheets

APPARATUS AND METHOD FOR OBSERVING AN EYE, AS WELL AS OCT-MODULE

SUMMARY

The invention relates to an apparatus for observing an eye, comprising an imaging device that is provided with a magnification unit and an observation unit, wherein the magnification unit has an objective lens for receiving observation light rays from the eye, and an optical coherence tomography (OCT) system comprising an OCT light source for emitting OCT light, splitting means for splitting the OCT light into a reference beam and a sample beam, and transferring means for directing the sample beam from the splitting means through the objective lens to the eye.

Optical coherence tomography (OCT) is a non-invasive technique for imaging subsurface tissue structure with accurate resolution. The reference beam is reflected by a reference object, such as a mirror, whereas the sample beam is guided to the sample, e.g. the retina of the eye. The interference between the backreflected reference and sample beams represents the thicknesses of different layers of the eye. The sample beam can be scanned along a line in the eye in order to obtain a cross-sectional image of the eye. OCT is generally carried out by using a OCT dedicated apparatus in combination with a computer.

WO 03/086180 describes an ophthalmological examination and/or treatment station. Instead of arranging several subunits exchangeably on an ophthalmological apparatus, the ophthalmological examination and/or treatment station is of a permanent modular design, i.e. it takes up the space of just one apparatus but makes it possible to achieve the functionality of a number of different apparatus. It comprises a lighting device, an observation device, an evaluation unit and a measuring system, and also a patient module to be arranged directly in front of the patient's eye. The measuring system and the lighting device are arranged remote from the patient and are connected to the patient module via optical fibres. The connection of the optical fibres to the patient module is made detachable, so that different measuring systems and lighting devices can be easily connected up, depending on which examinations or observations are to be performed.

The measuring system may be a Michelson interferometer-type optical system having a reference arm and a measuring arm. A so-called source beam issuing from a radiation source is divided into a reference beam and a measurement beam. This device may be integrated into an existing slit lamp for eye examination. The measurement beam, as free-space beam, can then be coupled either via beam splitters into the lighting beam path, in a microscope also via beam splitters into an observation beam path, or in the microscope objective or with a deflection mirror into a centre channel between two beam paths of a stereo microscope of the slit lamp. However, such incorporation into an existing slit lamp requires permanent structural modifications. These modifications lead to substantial reconstruction costs and therefore it is hardly economic, if at all, to retrofit an existing split lamp with such a measuring system. Moreover, the modifications to the slit lamp need to be carried out by its manufacturer or a specialised technical service. Consequently, the ophthalmologist is temporarily deprived of the slit lamp to be modified while most slit lamps are used on a daily basis.

An object of the invention is to provide an improved apparatus for observing the eye.

This object is achieved in that the OCT system comprises an OCT module that is detachably connected between the magnification unit and the observation unit. The OCT module according to the invention forms a unit that can be coupled to the optical system of an existing apparatus for the examination of an eye. The OCT module is detachably connected on either side to the magnification unit and the observation unit of the apparatus. The OCT module forms an add-on module, i.e. the OCT module can be added and removed as a module with respect to the existing apparatus for observing the eye. When the OCT module is mounted in place, both the sample beam that is directed to the eye and the backreflected light from the retina will pass through the objective lens during examination. The objective lens of the magnification unit is a part of the sample arm of the OCT system. The sample beam passes through the objective lens of the imaging device towards the observed eye during examination. The backreflections are branched off by the transferring means to the OCT system. The transferring means may be provided in the OCT module. The functionality of the existing apparatus for examination of the eye can therefore be extended with OCT without the need for redesign of the existing apparatus, i.e. without incurring substantial reconstruction costs. The costs are mainly limited to the initial purchasing costs of the OCT module as a separate unit. The modification of the existing apparatus is simple and relatively inexpensive. Possibly, the ophthalmologist himself can modify the existing apparatus.

A further advantage is that the dimensions of the apparatus according to the invention combining OCT and conventional eye observation, e.g. fundus or cornea, are considerably diminished compared to having two separate devices, one for OCT and another for said conventional eye observation.

It is noted that the magnification unit provided with the objective lens may have a magnifying factor that is less than 1, equal to 1 or greater than 1. The objective lens usually has a magnifying factor that is greater than 1. Then, the remainder of the magnification unit may have a magnifying factor that is less than 1, equal to 1 (i.e. light is let through without additional magnification) or greater than 1.

In an embodiment the magnification unit and the observation unit are aligned with respect to each other along an observation path, wherein the magnification unit has a rear face that faces towards the observation unit, and wherein the observation unit has a front face that faces towards the magnification unit, and wherein the rear face of the magnification unit and the front face of the observation unit are provided with mating connecting members which can be detachably connected to each other. When the OCT module is removed, the magnification unit and the observation unit can be connected to each other using a detachable connection. When the magnification unit and the observation unit are detached, the OCT module can be placed between them.

For providing a detachable connection between the OCT module and the magnification unit and the observation unit, it is possible that the OCT module is aligned along the observation path, wherein the OCT module has a front face that faces towards the magnification unit and a rear face that faces towards the observation unit, and wherein the front face of the OCT module is provided with a connecting member mating with the connecting member of the rear face of the magnification unit, and wherein the rear face of the OCT module is provided with a connecting member mating with the connecting member of the front face of the observation unit, and wherein the connecting members of the OCT module can be detachably connected to the mating connecting members of the magnification unit and the observation unit, respectively.

According to the invention the magnification unit and the OCT module are detachably connected to each other, and also the OCT module and the observation unit are detachably connected to each other. The detachable connections of the OCT module between the magnification unit and the observation unit of the imaging device or the mating connecting members can be constructed in various ways.

For example, the magnification unit and the OCT module comprise adjoining faces having a recess and a protrusion that is accommodated within the recess, wherein the recess is provided with engaging members for detachably engaging the protrusion accommodated in the recess. It is also possible that the OCT module and the observation unit comprise adjoining faces having a recess and a protrusion that is accommodated within the recess, wherein the recess is provided with engaging members for detachably engaging the protrusion accommodated in the recess. This type of detachable connections corresponds to a "standard" mounting that is generally located between the magnification unit and the observation unit. The "standard" mounting allows the OCT module to form an add-on module for many existing imaging devices. For example, the majority of the slit lamps already in use can be extended with the OCT module according to the invention.

In an embodiment, the OCT system comprises a reference arm in which the reference beam is guided to a reference object and a reflected reference beam is backreflected from the reference object, and a sample arm in which the sample beam is guided to the eye and a reflected sample beam is backreflected from the eye, wherein the OCT light source and the splitting means are optically connected for guiding the OCT light from the OCT light source to the splitting means, and the splitting means are optically connected to the reference arm, the sample arm and an optical detector. The sample arm is at least partially mounted within the imaging device such that the sample beam is guided through the objective lens to the eye.

The OCT light source can be configured in various ways. For example, the OCT light source is arranged for emitting OCT light comprising a wavelength of 700-2000 nm, preferably 700-1500 nm. The broadband source may include a source that emits a steady spectrum continuously, such as super luminescent diodes (SLD), Ti:Sapphire sources or other, and a source that can tune the frequency of its spectrum rapidly such as femto-second lasers or other types of tuneable lasers.

The OCT light source is optically connected to the splitting means, i.e. the OCT light can be guided to the splitting means. The optical connection may comprise optical fibers and/or other components to control various parameters such as power, polarization and other. Optical isolators may be used to protect the OCT light source from undesired backreflected light. It is also possible that the optical connection includes a circulator that increases the light efficiency of the OCT system and protects the OCT light source from undesired backreflected light.

The splitting means split the light from the OCT light source into two beams: the reference and the sample beam. The splitting ratio defining the energy distributed in the two beams are generally 50/50, 30/70 or 10/90. However, any other values are possible as well. Backreflected light from the reference object and the sample object are recombined to an optical signal leading to the optical detector. The optical signal is subject to interference. For example, the splitting means are fiber based or open-air configured. In an open air configuration collimating means are used to define the light beam that propagates through the open air. These collimating means are placed in front of the splitting means.

The reference arm may comprise a transferring means to guide the reference beam to the reference object. For example, these transferring means are adapted for controlling various parameters, such as optical power, dispersion and polarization. The reference object, such as a reference mirror, reflects the reference beam back to the splitting means. In most configurations the first part of the reference beam is fiber based. In that case, collimating means are used as a link between the fiber based and open-air setup. The portion between the splitting means and the reference object is usually referred to as "reference arm" of the OCT system.

The sample arm may comprise transferring means to guide the sample beam to the tissue of the eye. According to the invention the objective lens of the imaging device is a part of the transferring means of the sample arm. The structure of the tissue of the eye includes different layers. The boundaries between these layers imply changes in the index of refraction, which results in variable reflections. Backreflected light from the tissue is guided back through the objective lens toward the splitting means. Similar to the reference arm, the sample arm usually has an optical fiber that guides the sample beam from the splitting means to a collimating means. These collimating means are the link between the fiber based and open-air parts of the sample arm and are located behind the objective lens. The open-air portion of the sample arm comprises the objective lens. Backreflected light from the eye is guided via the objective lens to the collimating means and subsequently propagates through the sample optical fiber back to the splitting means. The portion between the splitting means and the sample object is usually referred to as "sample arm" of the OCT system.

The optical detector may be constructed in various ways. In an embodiment the optical detector is adapted for converting the optical signal detected by the optical detector into an electrical signal, wherein the electrical signal is transported to a data processing unit. For example, the optical detector comprises a spectrograph or a 'single' detector. The spectrograph can be used in combination with a continuous broadbanded source such as a SLD, whereas a single detector can be used in combination with a sweptsource. The spectrograph typically has transferring means, diffraction means and a linescan camera to convert the optical signal into an electrical signal, but other configurations are possible as well. The electrical signal is transported to a data processing unit. For example, the data processing unit is a computer system, such as a personal computer (PC), laptop, personal digital assistant (PDA) or other. The data processing unit may visualise the electrical signals to a cross sectional image of the observed eye.

In an embodiment, the OCT light source, the splitting means and the reference arm including the reference object are mounted in a control box, wherein the sample beam is guided from the splitting means in the control box to the OCT module by an optical fibre. The control box can be placed remote from the apparatus for observing the eye, which includes the OCT module. The ophthalmologist can easily add and remove an OCT module when desired.

In an embodiment the OCT module comprises scanning means. The scanning means are accommodated inside the OCT module, i.e. the scanning means are located relatively close to the transferring means for directing the sample beam through the objective lens to the eye. This widens the scan area. It is noted that the OCT module may comprise a plurality of components that are mounted together. For example, the scanning means are received within a housing that is attached to the OCT module.

The transferring means for directing the sample beam from the splitting means through the objective lens to the eye may comprise a beam splitter for reflecting the sample beam into the direction of the observation path. The beam splitter is mounted in the OCT module.

It is possible that the observation unit comprises an eyepiece. The sample beam is introduced into the imaging device between the eyepiece and the objective lens. For example, the eyepiece comprises a (bio)microscope. An ophthalmologist may examine the eye by looking through the eyepiece.

In an embodiment, the observation unit comprises a digital camera, wherein the sample beam is introduced into the imaging device between the digital camera and the objective lens. Thus, the image which can be viewed through the eyepiece can be stored on a storage device or shown on a screen. For example, this image relates to the anterior segment or posterior segment of the eye.

In an embodiment the apparatus comprises an illumination system for emitting illumination light to the eye. When the illumination system is configured for projecting a slit of illumination on the eye, the apparatus constitutes a slit lamp. The slit of illumination may have a variable width. A slit lamp is commonly used for the examination of the anterior segment of the eye. Generally, any ophthalmologist disposes of a slit lamp. According to this embodiment an existing slit lamp can be easily modified to include OCT functionality by passing the sample beam through the objective lens of the imaging device of the slit lamp. The OCT system can be added as a module to newly manufactured slit lamps and also to slit lamps already in use.

The illumination system of a slit lamp can be constructed in various ways. For example, the illumination system is mounted in a housing column extending transversely with respect to the observation path. The illumination system may then comprise transferring means for transferring the illumination light emitted by the light source to the eye.

It is possible that the apparatus comprises focusing means for focusing the illumination light and/or the sample beam on the fundus of the eye. For example, the focusing means comprise an ocular lens. In proper position, the focusing means guide all light rays from the illumination system impinging on its proximal side into the eye and focus the slit object in the illumination column onto the retina. Simultaneously, the sample beam which is directed through the observation system impinges on the proximal side of the focusing means, is projected into the fundus and when aligned correctly focused on the retina. Correct alignment implicates that the image plane of the slit object in the illumination column and the fibre tip of the sample arm collide at the same plane. The focusing means allow OCT imaging of the fundus of the eye, in particular the retina. Moreover, the apparatus, such as a slit lamp or operation microscope, can be used for observing the posterior segment of the eye.

It is noted that the focusing means are entirely optional, because there are several applications that do not require focusing on the fundus. For example, it is also possible that an ophthalmologist desires to observe and/or obtain an OCT image of the anterior segment of the eye, for example the cornea.

The invention is not limited to any type of OCT—the OCT system according to the invention may apply, for example, Spectral Domain OCT (also referred to as Fourier Domain OCT and Frequency Domain OCT), or Time Domain OCT.

The invention also relates to an OCT module for an apparatus for observing an eye, such as a slit lamp or operation microscope, which OCT module comprises transferring means for transferring a sample beam from a first direction into a second direction, and which OCT module comprises a front face and a rear face, the front face being provided with a first connecting member, and the rear face being provided with a second connecting member mating with the first connecting member, and wherein the first and second connecting members can be detachably connected to a connecting member corresponding to the second and first connecting member, respectively. For example, one of said faces is provided with a recess and the other with a corresponding protrusion. This OCT module can be connected to a generally "standard" mounting of a slit lamp.

The invention further relates to a method for observing an eye, comprising receiving observation light rays from an eye at an objective lens of an imaging device, emitting OCT light from an OCT light source of an optical coherence tomography (OCT) system, splitting the OCT light into a reference beam and a sample beam, and guiding the sample beam through the objective lens to the eye.

BRIEF DESCRIPTION OF THE FIGURES

The invention will now be explained in more detail with reference to an exemplary embodiment shown in the accompanying drawing.

DETAILED DESCRIPTION

Figure 1:
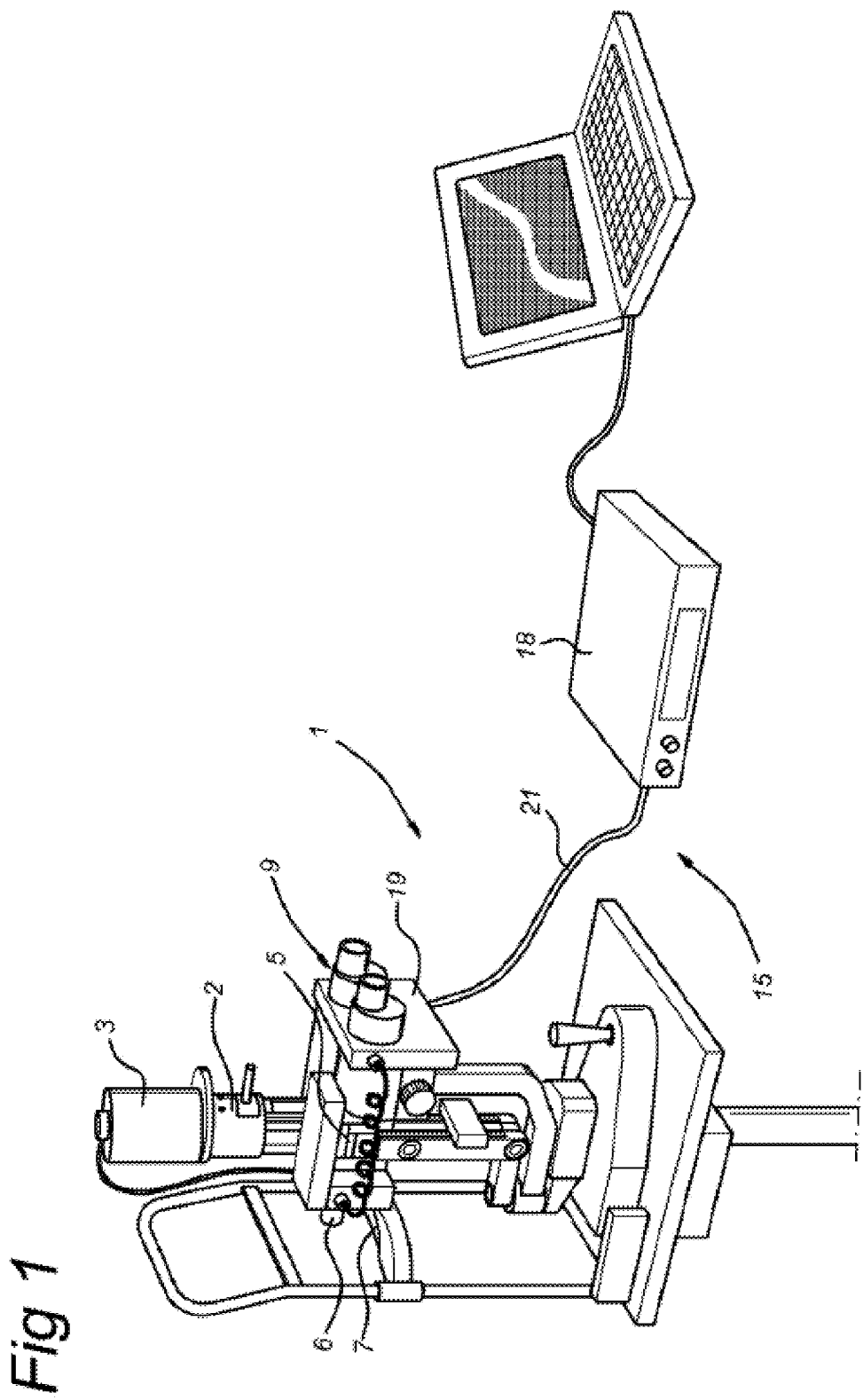
FIG. 1 shows a perspective view of an apparatus for observing an eye.

The exemplary embodiment of an apparatus for observing an eye is denoted in its entirety by 1. The apparatus 1 according to this exemplary embodiment constitutes a slit lamp. The slitlamp 1 facilitates an examination of the anterior segment of a human eye, which includes the sclera, conjunctiva, iris, natural crystalline lens and cornea. A slit lamp is widely used in ophthalmoscopic applications. The slitlamp 1 comprises an illumination system 2 provided with a light source 3 for emitting an illumination light. For example, the light source 3 can be focused for emitting a slit of illumination. The slitlamp 1 comprises a support frame 7 for supporting the head of a patient (not shown). The eye of the patient is facing toward the illumination system 2 during examination, so that the slit of illumination is projected onto the eye.

In this exemplary embodiment the illumination system 2 is mounted within a housing column that extends substantially vertically. As a result, the illumination system 2 has transferring means 5 for transferring the illumination light emitted by the light source 3 to the eye of the patient. Of course, the type, construction and/or orientation of the illumination system may be different.

Figure 2:
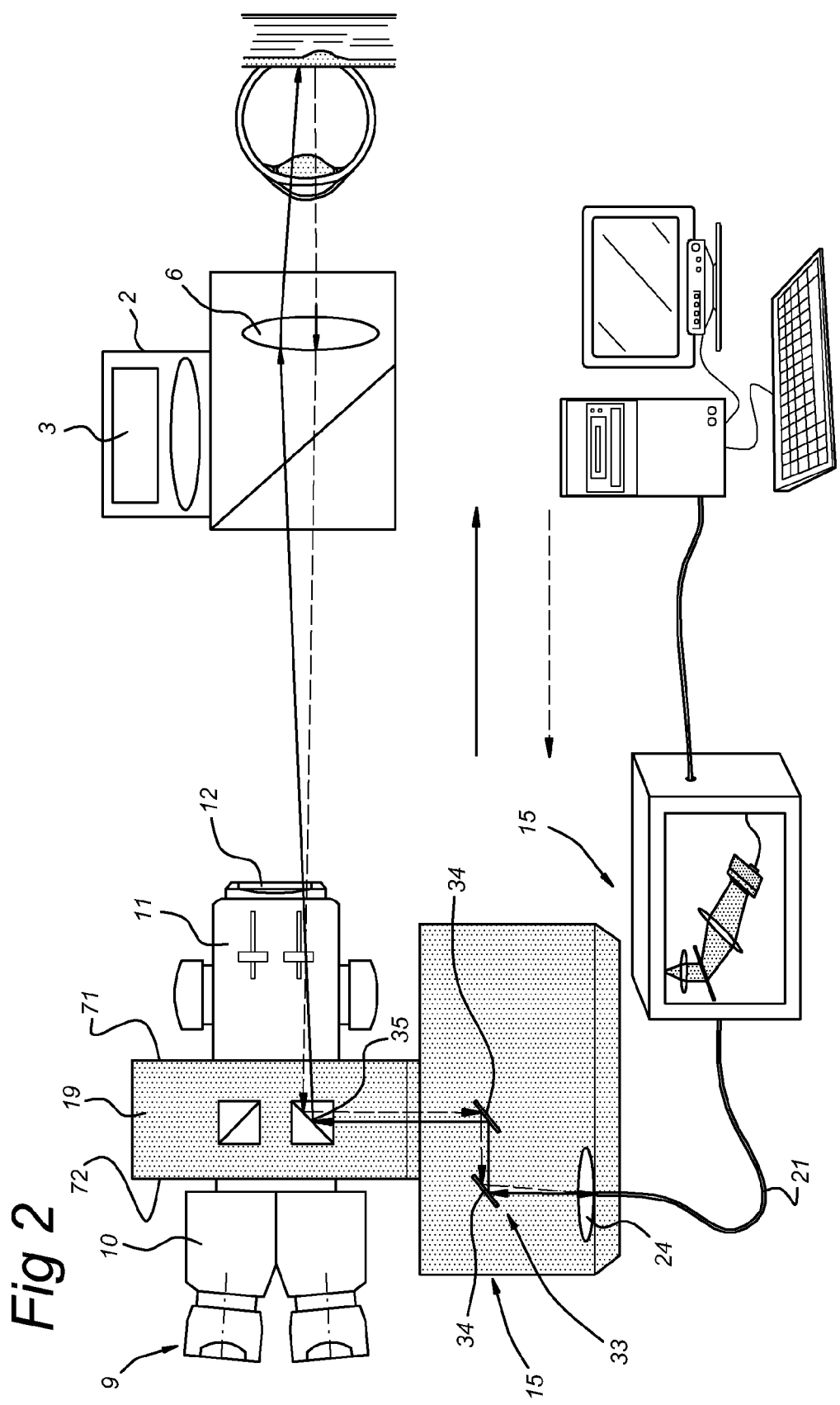
FIG. 2 shows a diagrammatical top view of the apparatus shown in FIG. 1.

The apparatus 1 comprises an imaging device 9 that is provided with an objective lens 12 for receiving observation light rays from the eye (see FIG. 2). The objective lens 12 is located at the distal end of the imaging device 9—the observation light rays from the eye enter the imaging device 9 through the objective lens 12. The objective lens 12 is exposed at the outer side of the imaging device 9 facing the support frame 7. In this exemplary embodiment the imaging device 9 has an eyepiece unit 10 and a magnification unit 11. The magnification unit 11 is provided with the objective lens 12.

Obviously, the eyepiece unit 10 of the imaging device 9 can be replaced by any other observation unit, such as a digital camera (not shown). It is also possible that the eyepiece unit 10 is combined with a digital camera (not shown).

The apparatus 1 shown in the figures comprises focusing means 6 for focusing the illumination light and sample beam on the fundus of the eye. The focusing means may include an ocular lens 6 having an image plane that is focused on the fundus of the eye during examination. The ocular lens 6 focuses any light rays impinging from its proximal side onto the fundus of the eye. The optical axis of the ocular lens 6 runs along the observation path of the imaging device 9 extending between the eye and the objective lens 12. The optical axis of the ocular lens 6 is substantially parallel to or coincides with this observation path. Thus, it is possible to examine an image of the fundus, in particular the retina of the eye.

The apparatus 1 according to the invention comprises an optical coherence tomography (OCT) system 15. The OCT system 15 facilitates optical coherence tomography—an interferometric, non-invasive imaging technique with millimeter penetration and (sub)micrometer resolution. For example, the penetration depth into a human eye is approximately 2-3 mm depending on the tissue properties and the design of the OCT system. The OCT system 15 provides in vivo cross-sectional imaging of superficial tissues of the eye. For example, a cross-sectional image of the retina can be obtained, which allows e.g. visualisation of various retinal layers, measurement of the retinal thickness and the retinal nerve fibre layer. The screening possibilities of the slitlamp 1 are expanded as a result of incorporating the OCT system 15. After all, the apparatus 1 according to this embodiment constitutes a slit lamp including OCT functionality.

Figure 4:
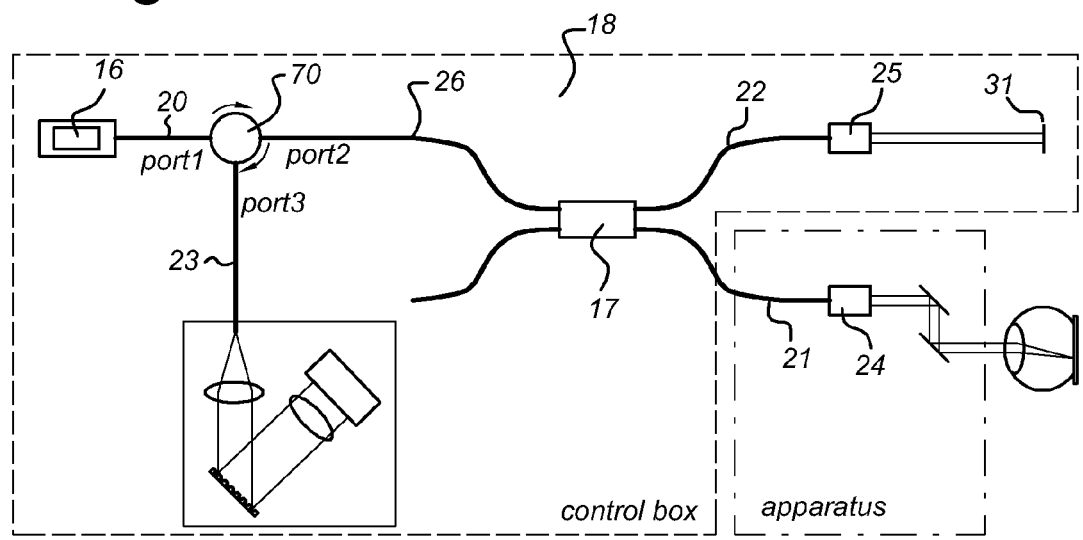
FIG. 4 shows a diagrammatical view of the OCT system of the apparatus shown in FIG. 1.

In this exemplary embodiment, the OCT system 15 comprises an OCT light source 16 for emitting OCT light. The OCT light source 16 is mounted in a control box 18 (see FIG. 4). A circulator 70 having three ports is provided. The OCT light source 16 is connected using an OCT light optical fibre 20 to the first port of a circulator 70. The circulator 70 directs the OCT light from the first port to the second port and into an optical fibre 26, which carries the OCT light to splitting means 17. The splitting means 17 are adapted for splitting the OCT light into a reference beam and a sample beam. For example, the splitting means 17 comprise a beam splitter.

In this exemplary embodiment, a reference beam optical fibre 22 transports the reference beam to a reference beam collimator 25. The reference beam collimator 25 directs the reference beam in open air to a reference mirror 31. The open air portion of the reference beam allows controlling of various parameters, such as optical power, dispersion and polarisation. The backreflections from the reference mirror 31 are received by the reference beam collimator 25 and subsequently guided through the reference beam optical fibre 22 back to the splitting means 17.

The sample beam is carried by a sample beam optical fibre 21 to a sample beam collimator 24. As shown in FIG. 2 the OCT system also comprises OCT transferring means 33 for transferring the sample beam originating from the sample beam collimator 24 through the objective lens 12 to the eye. In this exemplary embodiment the OCT transferring means 33 comprise two Galvano mirrors 34 and a beam splitter 35 for at least partially directing the sample beam into the observation path of the imaging device 9. The Galvano mirrors 34 form scanning means.

The sample beam of the OCT light impinges on the focusing means 6, which focuses the sample beam onto the fundus of the eye. Thus, the sample beam is reflected by the fundus. The boundaries between different retinal layers give rise to respective backreflections that propagate back through the eye, the focusing means 6, and the objective lens 12 of the imaging device 9 until they are received by the sample beam collimator 24. The reflected sample beam passes through the OCT transferring means 33 and the sample beam optical fibre 21 to the splitting means 17.

The reflected reference beam and the reflected sample beam are recombined in the splitting means 17, i.e. they interfere constructively or destructively with each other. The interference of the reflected reference beam and reflected sample beam causes an optical detection signal that is guided by the optical fibre 26 to the second port of the circulator 70, which directs the optical detection signal to the third port. The third port of the circulator 70 is optically connected by a detection optical fibre 23 to an optical detector.

The optical detector is, for example, a spectrograph. It may be adapted for converting the optical detection signal detected by the optical detector into an electrical signal. The electrical signal can then be transported to a data processing unit. For example, the data processing unit is a computer system, such as a personal computer (PC), laptop, personal digital assistant (PDA) or other. The data processing unit may visualise the electrical signals from the spectrograph.

In this exemplary embodiment, the OCT light source 16, the circulator 70, the splitting means 17, the reference arm 22, 25, 31 and the detector arm 26, 23 including the spectrograph are accommodated inside a control box 18. The sample beam optical fibre 21 extends from the control box 18 to an OCT module 19. The sample beam collimator 24 is mounted within the OCT module 19.

Figure 3A:
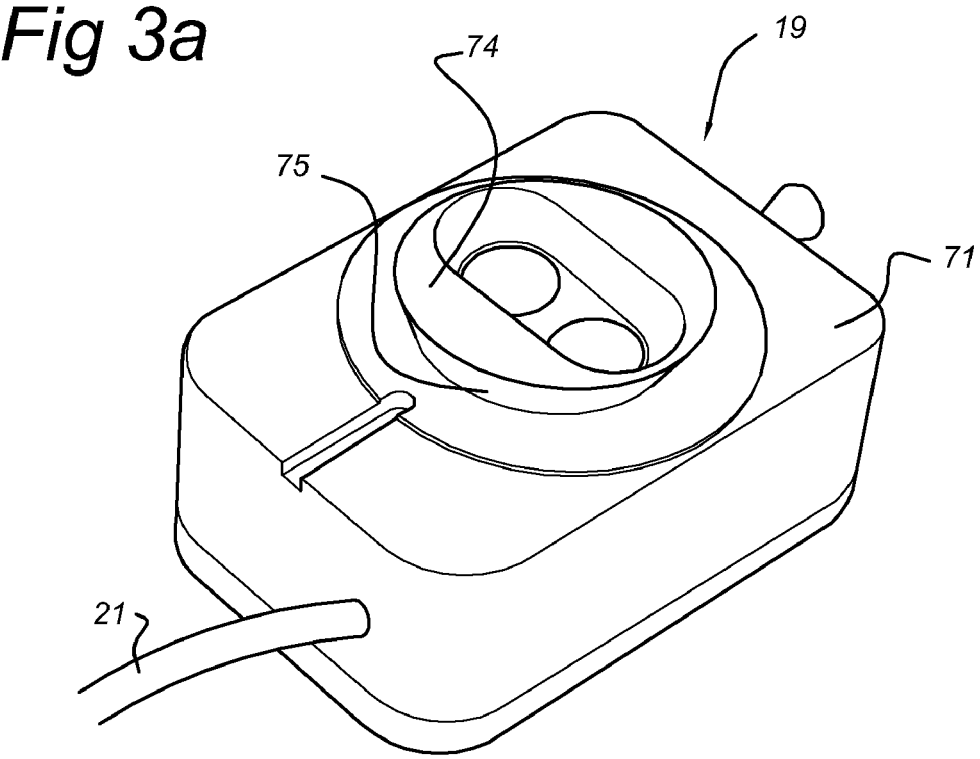
FIG. 3a, 3b show perspective views of an OCT module according to the invention.
Figure 3B:
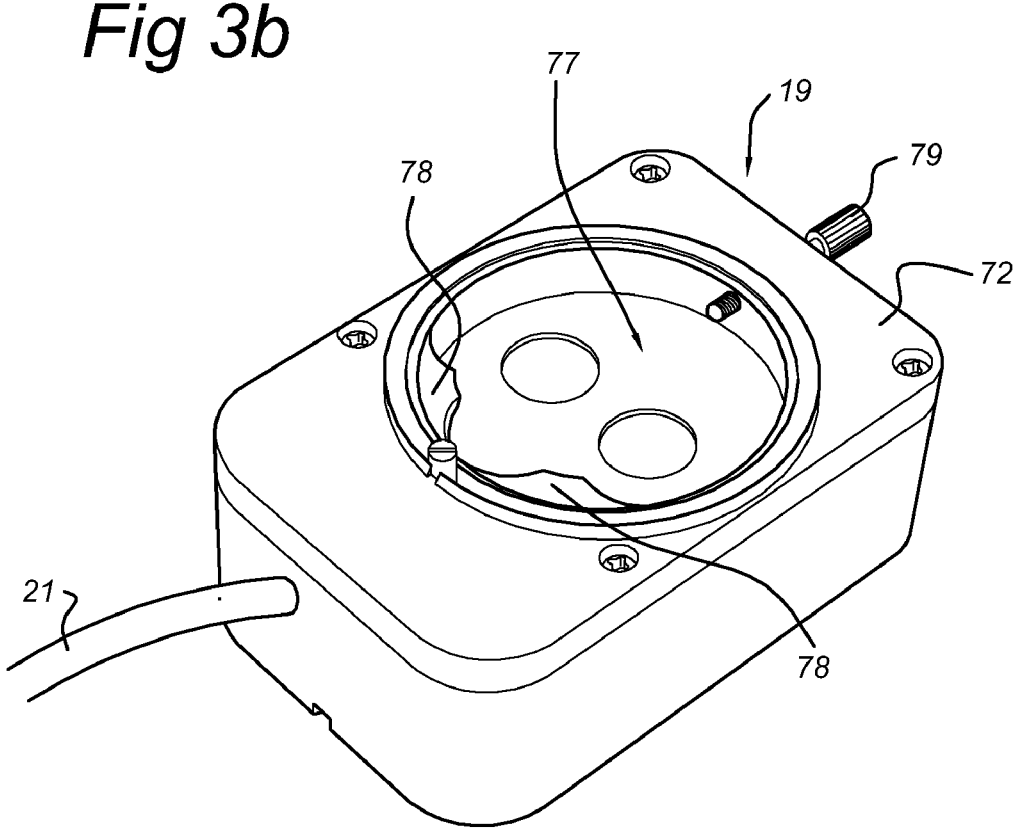

The OCT module 19 is detachably connected between the objective lens 12 and the eyepiece unit 10 of the imaging device 9 (see FIG. 1). The OCT module 19 is shown in more detail in FIGS. 3a and 3b. The OCT module 19 comprises a front face 71 and a rear face 72. The front face 71 is provided with a ring-shaped protrusion 74 having a conical outer surface 75. The front face 71 adjoins against a rear face of the magnification unit 11. The shape of the rear face of the magnification unit 11 corresponds to the rear face 72 of the OCT module 19 shown in FIG. 3b.

The rear face 72 of the OCT module 19—and the rear face of the magnification unit 11—comprises a recess 77. The recess 77 is provided with engaging members for detachably engaging the protrusion 74 of the OCT module 19 when accommodated in the recess 77. The engaging members include two hook members 78 and a screw 79. First, the underside of the protrusion 74 is put behind the hook members 78. Then, the OCT module 19 is manipulated such that its front face 71 adjoins substantially flat against the rear face of the magnification unit 11. The screw 79 is screwed down for securing the detachable connection.

The rear face 72 of the OCT module 19 is placed against the front face of the eyepiece unit 10. The detachable connection between the OCT module 19 and the eyepiece unit 10 is identical to the detachable connection between the OCT module 19 and the magnification unit 11.

When the OCT module 19 is installed, it is possible to use the slit lamp 1 for measuring the respective thicknesses of different retinal layers at a specific location of the retina. The sample beam may be scanned along a line on the retina, i.e. the sample beam is displaced in relatively small steps over the retina. The resulting optical detection signals may be constructed together to form a cross sectional image of the retina.

An additional light source can be used for emitting visible light into the OCT system (not shown). Then, the scanning line on the retina can be observed simultaneously using the eyepiece 10 and/or a digital imaging unit (not shown) of the imaging device 9. The apparatus 1 provides both a cross-sectional image of the retina obtained by the OCT scan and a frontal image of the retina indicating the scanning line used. Thus, the ophthalmologist not only obtains the cross-sectional image of the retina, but also has information of the exact location where the cross-section has been taken.

Figure 5:
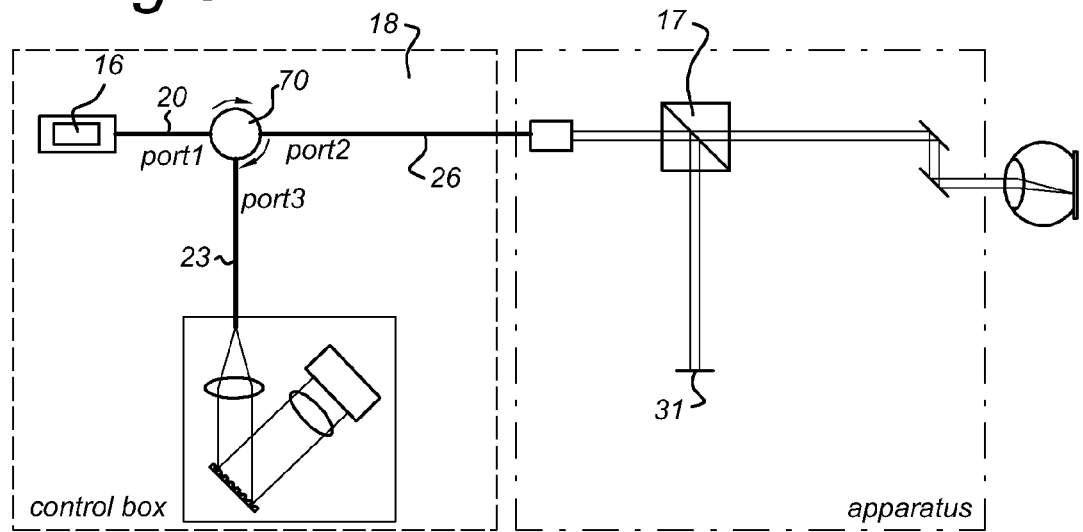
FIG. 5 shows a diagrammatical view of an alternative OCT system.

FIG. 5 shows an alternative embodiment of the OCT system. In this embodiment the OCT light source 16, the circulator 70 and the detection arm 26, 23 including the spectrograph are mounted within the control box 18. The splitting means 17, the reference arm and the sample arm are located within the OCT module 19.

When the OCT light source is switched off, the apparatus 1 according to this embodiment can be used as a conventional slit lamp. The ophthalmologist can examine the anterior segment of the eye and the fundus or posterior segment of the eye using the ocular lens 6.

Of course, the invention is not limited to the exemplary embodiment shown in the figures. It will be apparent to the skilled person that many modifications of this exemplary embodiment are possible without departing from the scope of the invention. For example the OCT module can be used as an add-on module not only for a slit lamp, but for any ophthalmic apparatus.

The invention claimed is:

1. An apparatus for observing an eye, comprising: an imaging device (9) that is provided with a magnification unit (11) and an observation unit (10), wherein the magnification unit (11) has an objective lens (12) for receiving observation light rays from the eye, and an optical coherence tomography (OCT) system (15) comprising an OCT light source (16) for emitting OCT light, splitting means (17) for splitting the OCT light into a reference beam and a sample beam, and transferring means (33) for directing the sample beam from the splitting means (17) through the objective lens (12) to the eye, wherein the OCT system (15) comprises an OCT module (19) that is detachably connected between the magnification unit (11) and the observation unit (10), wherein the magnification unit (11) and the observation unit (10) are aligned with respect to each other along an observation path, and wherein the magnification unit (11) has a rear face that faces towards the observation unit (10), and wherein the observation unit (10) has a front face that faces towards the magnification unit (11), and wherein the rear face of the magnification unit (11) and the front face of the observation unit (10) are provided with mating connecting members which can be detachably connected to each other, and wherein the OCT module (19) is aligned along the observation path, and wherein the OCT module (19) has a front face (71) that faces towards the magnification unit (11) and a rear face (72) that faces towards the observation unit (10), and wherein the front face (71) of the OCT module (19) is provided with a connecting member mating with the connecting member of the rear face of the magnification unit (11), and wherein the rear face (72) of the OCT module (19) is provided with a connecting member mating with the connecting member of the front face of the observation unit (10), and wherein the connecting members of the OCT module (19) can be detachably connected to the mating connecting members of the magnification unit (11) and the observation unit (10), respectively.

2. The apparatus according to claim 1, wherein the OCT system (15) comprises a reference arm in which the reference beam is guided to a reference object (31) and a reflected reference beam is back reflected from the reference object (31), and a sample arm in which the sample beam is guided to the eye and a reflected sample beam is back reflected from the eye, wherein the OCT light source (16) and the splitting means (17) are optically connected for guiding the OCT light from the OCT light source (16) to the splitting means (17), and the splitting means (17) are optically connected to the reference arm, the sample arm and an optical detector.

3. The apparatus according to claim 2, wherein the OCT light source (16), the splitting means (17) and the reference arm including the reference object (31) are mounted in a control box (18), and wherein the sample beam is guided from the splitting means (17) in the control box (18) to the OCT module (19) by an optical fibre (21).

4. The apparatus according to claim 1, wherein the OCT module comprises scanning means (34, 35).

5. The apparatus according to claim 1, wherein the transferring means (33) comprise a beam splitter (35) for reflecting the sample beam into the direction of the observation path.

6. The apparatus according to claim 1, wherein the observation unit comprises an eyepiece unit (10) and/or digital camera.

7. The apparatus according to claim 1, wherein the apparatus comprises an illumination system (2) for emitting illumination light to the eye, such as for projecting a slit of illumination on the eye.

8. The apparatus according to claim 1, wherein the apparatus (1) comprises focusing means (6) for focusing the sample beam on the fund us of the eye.

9. An apparatus for observing an eye, comprising: an imaging device (9) that is provided with a magnification unit (11) and an observation unit (10), wherein the magnification unit (11) has an objective lens (12) for receiving observation light rays from the eye, and an optical coherence tomography (OCT) system (15) comprising an OCT light source (16) for emitting OCT light, splitting means (17) for splitting the OCT light into a reference beam and a sample beam, and transferring means (33) for directing the sample beam from the splitting means (17) through the objective lens (12) to the eye, wherein the OCT system (15) comprises an OCT module (19) that is detachably connected between the magnification unit (11) and the observation unit (10), wherein the magnification unit (11) and the OCT module (19) comprise adjoining faces having a recess (77) and a protrusion (74) that is accommodated within the recess (77), wherein the recess (77) is provided with engaging members (78, 79) for detachably engaging the protrusion (74) accommodated in the recess (77).

10. An apparatus for observing an eye, comprising: an imaging device (9) that is provided with a magnification unit (11) and an observation unit (10), wherein the magnification unit (11) has an objective lens (12) for receiving observation light rays from the eye, and an optical coherence tomography (OCT) system (15) comprising an OCT light source (16) for emitting OCT light, splitting means (17) for splitting the OCT light into a reference beam and a sample beam, and transferring means (33) for directing the sample beam from the splitting means (17) through the objective lens (12) to the eye, wherein the OCT system (15) comprises an OCT module (19) that is detachably connected between the magnification unit (11) and the observation unit (10), wherein the OCT module (19) and the observation unit (10) comprise adjoining faces having a recess (77) and a protrusion (74) that is accommodated within the recess (77), wherein the recess (77) is provided with engaging members (78, 79) for detachably engaging the protrusion (74) accommodated in the recess (77).

* * * * *